United States Patent [19]

Bogert et al.

[11] Patent Number: 5,713,876
[45] Date of Patent: Feb. 3, 1998

[54] CATHETER RELEASE MECHANISM

[75] Inventors: David L. Bogert, Plainville, Conn.; Thomas K. Sutton, Carrollton, Tex.

[73] Assignee: Johnson & Johnson Medical, Inc., Arlington, Tex.

[21] Appl. No.: 483,949

[22] Filed: Jun. 7, 1995

[51] Int. Cl.$^6$ .................................................. A61M 5/00
[52] U.S. Cl. ........................................... 604/243; 604/187
[58] Field of Search .................................. 604/243, 264, 604/187, 164–170, 240, 241, 242

[56] References Cited

U.S. PATENT DOCUMENTS

| | | | |
|---|---|---|---|
| 4,762,516 | 8/1988 | Luther et al. | 604/164 |
| 4,804,371 | 2/1989 | Vaillancourt | 604/198 |
| 4,832,696 | 5/1989 | Luther et al. | 604/164 |
| 4,834,718 | 5/1989 | McDonald | 604/195 |
| 4,917,669 | 4/1990 | Bonaldo | 604/164 |
| 4,944,725 | 7/1990 | McDonald | 604/164 |
| 4,950,252 | 8/1990 | Luther et al. | 604/198 |
| 4,964,854 | 10/1990 | Luther | 604/166 |
| 4,978,344 | 12/1990 | Dombrowski et al. | 604/198 |
| 5,084,023 | 1/1992 | Lemieux | 604/167 |
| 5,084,030 | 1/1992 | Byrne et al. | 604/198 |
| 5,127,905 | 7/1992 | Lemieux | 604/164 |
| 5,201,716 | 4/1993 | Richard | 604/187 |
| 5,205,829 | 4/1993 | Lituchy | 604/164 |
| 5,215,528 | 6/1993 | Purdy et al. | 604/164 |

Primary Examiner—John D. Yasko
Attorney, Agent, or Firm—Joseph F. Shirtz

[57] ABSTRACT

A catheter insertion device incorporating a simple lever and clip structure which will safely lock a catheter hub of a catheter assembly to a normally disposable cannula housing and guard structure and which, in a simple mode, enables separation of the catheter hub from the cannula assembly or structure upon retraction and protective guarding of the used cannula. Specifically, an aspect resides in providing the lever release clip for a safety catheter which upon unlocking and releasing of the catheter hub concurrently pushes the catheter hub off a nose guard of the cannula assembly, while enabling a physician or clinical personnel to release the catheter by employing only one hand. A further embodiment is adapted to enable separation between the catheter hub of a flexible catheter and the needle or cannula arrangement of a catheter insertion device by simply manipulating a lever arranged on a cannula structure or nose guard thereof by simply pushing against a push-tab element.

13 Claims, 12 Drawing Sheets

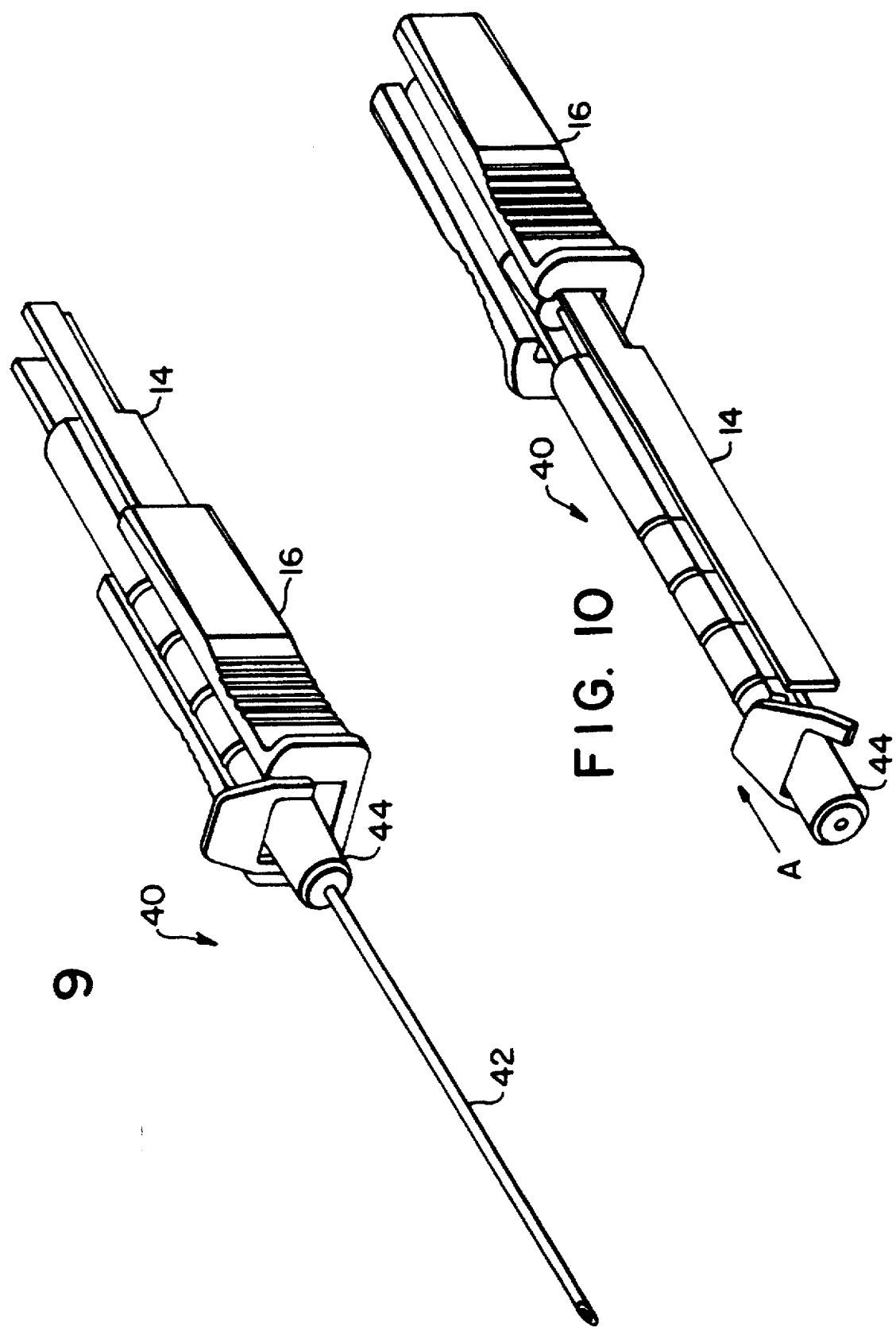

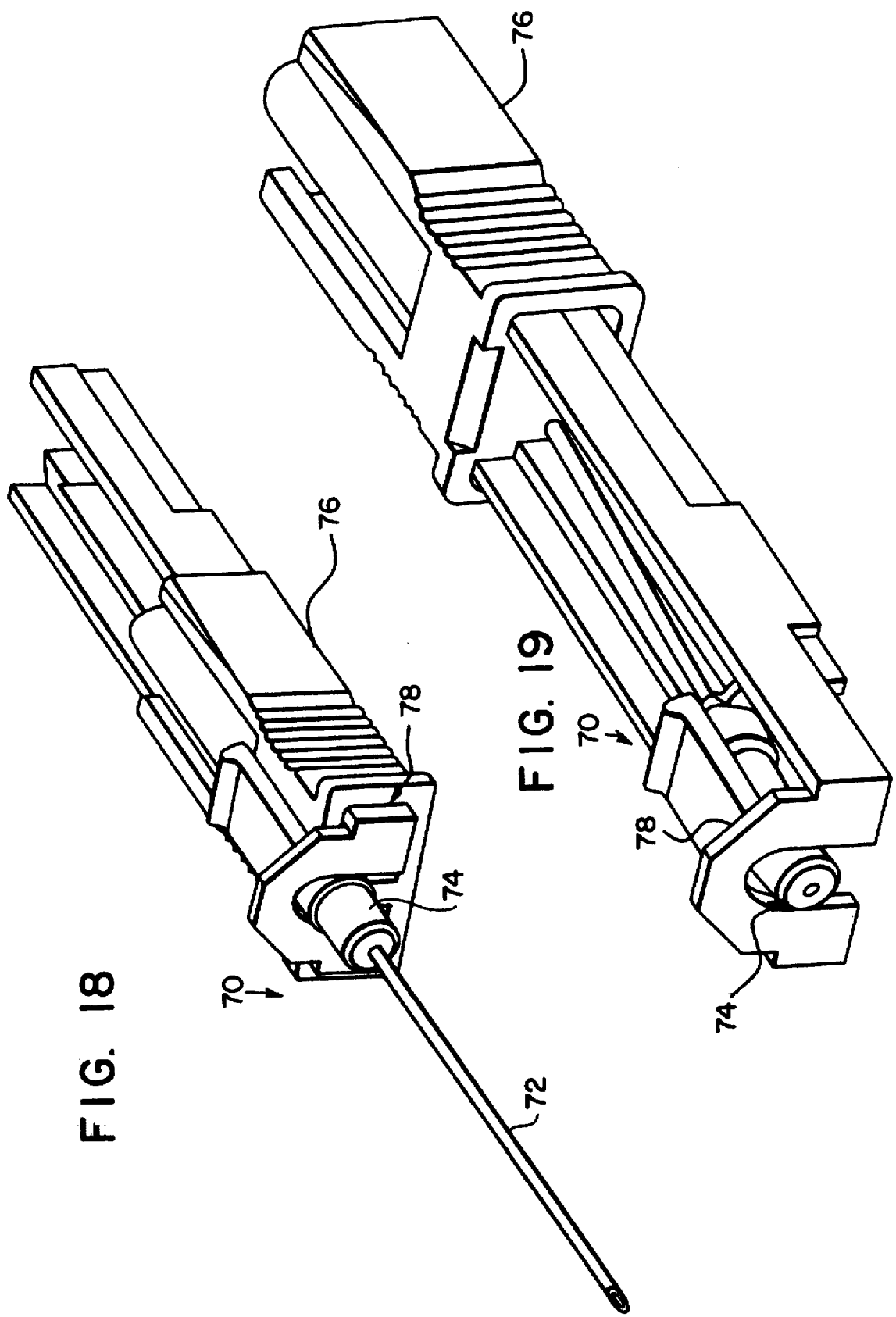

CATHETER RELEASE MECHANISM

BACKGROUND OF THE INVENTION

1. Field of the Invention

The present invention relates, in general, to intravenous catheter insertion devices, and in particular relates to a catheter insertion device incorporating a simple lever and clip structure which will safely lock a catheter hub of a catheter assembly to a normally disposable cannula housing and guard structure and which, in a simple mode, enables separation of the catheter hub from the cannula assembly or structure upon retraction and protective guarding of the used cannula. Specifically, an aspect of the invention resides in providing the lever release clip for a safety catheter which upon unlocking and releasing of the catheter hub concurrently pushes the catheter hub off a nose guard of the cannula assembly, while enabling a physician or clinical personnel to release the catheter by employing only one hand. The invention is further adapted to enable separation between the catheter hub of a flexible catheter and the needle or cannula arrangement of a catheter insertion device by simply manipulating a lever arranged on a cannula structure or nose guard thereof by simply pushing against a push-tab element.

The utilization of clinical apparatus in which pointed hollow needles or cannulas are employed in order to puncture the skin of a patient, and especially catheters utilizing such needles to effectuate venipunctures, is well known in the medical art and is widely practiced by physicians and clinical personnel for the purpose of injecting fluids and drugs directly into the bloodstream of patients. Additionally, during surgical operations or procedures it may be frequently required that whole blood transfusions and parenteral fluids be administered to a patient undergoing such surgical procedures. Basically, as is well known and has been employed for a considerable length of time, the introduction of such fluids into the cardiovascular systems of patients has necessitated the forming of a venipuncture utilizing a hollow rigid needle having a proximal attachment site for a fluid connection which is adapted to interconnect the needle with a source of intravenously administered fluids.

The foregoing method of administering fluids to patients through venipuncture has been subject to some rather serious problems in the administration of fluids to patients in this medical technology. Thus, a primary concern which had to be addressed resided in the inherent rigidity of the needle, the latter of which is normally constituted of surgical-quality steel, and while inserted into the vein of a patient necessitated the needle to be maintained for reasons of safety in a fixed position at the general site of the venipuncture throughout the duration of fluid administration or transfusion, whereby such a procedure could conceivably consume a considerable length of time. In addition to the foregoing, at times it has been necessary to periodically draw blood samples and/or successively administer intravenous fluids to a patient, thus requiring the patient to be subjected to a series or plurality of venipuncture, each administered at a specific time and at different sites on the body, resulting in a relatively traumatic experience for patients in view of such repeated and somewhat painful and unpleasant venipunctures.

In order to ameliorate or possibly even eliminate the foregoing problems in the medical technology, it has been more recently the practice to introduce a flexible tubular catheter of a low-friction material, such as a silastic or Teflon into the vein of a patient and to permit the catheter tube to remain in such a position over lengthier periods of time for purposes of; for example, periodically administering fluids, including parenteral fluids, blood/plasma transfusions, medications in liquid form and also for the collection of blood samples and the like. In this manner, the previously encountered trauma, extravasation, and infiltration caused by repeated venipuncture have been largely avoided, and the danger and discomfort to a patient of leaving a rigid needle in the body for a prolonged period of time has been generally overcome. Thus, in order to position the distal end of such a flexible catheter tube within the body cavity of a patient, such as a vascular cavity or vein, there is normally employed a cannula or hollow sharp-tipped needle for the purpose of forming the venipuncture. Thereafter, the flexible catheter tube, which is telescopically and slidably coaxially mounted on the outer circumference of the cannula or hollow needle so as to extend sleeve-like thereabout is advanced along the length of the needle into the vein subsequent to the needle having formed the venipuncture. Thereafter, the needle is adapted to be withdrawn from the interior of the catheter tube, while permitting the latter to remain within the body of the patient at the site of the venipuncture, and the needle is suitably discarded.

Inasmuch as the needle which has been previously positioned in the body of the patient upon forming the venipuncture may have been exposed to infectious agents; for instance, such as a patient infected with the Acquired Immune Deficiency Syndrome (AIDS) which is frequently or practically always ultimately fatal in nature, or other dangerous infectious conditions such as hepatitis, there is present the danger or hazard that the clinical personnel may inadvertently or accidentally jab or stick themselves with the used needle after withdrawal from the body of the patient, with the possibility of infection or even death resulting therefrom.

Heretofore, in order to release the structure which contains the used retracted needle or cannula from a lock on a catheter hub, the latter of which remains attached to a flexible catheter tube extending into the site of the puncture in the patient's body, it was frequently necessary for the clinician or physician to employ both hands in order to implement the separating operation between the catheter hub and used cannula structure so as to enable the subsequent attachment of a complementary Luer lock fitting to the Luer lock lug on the catheter hub for enabling the introduction of quantities of a parenteral fluid, supply of blood/plasma, or other medications to the patient in an intravenous procedure. Frequently, this necessitated that the clinical personnel was required to carry out, almost simultaneously or in rapid succession, two or three procedural steps, rendering the steps difficult to implement without the use of both hands, and possibly, upon occasion, even necessitating that one of the steps be delayed pending the completion of preceding steps in the separating of the catheter and cannula components.

2. Discussion of the Prior Art

Thus, U.S. Pat. No. 4,762,516 to Luther et al. discloses the retraction of a used needle or cannula into a protective housing. However, this necessitates the further procedure of having to release a catheter while essentially employing two hands.

Although other publications disclose various structures and methods for releasing catheters and their catheter hub structures from cannula assemblies while the cannulas have been retracted into a clinical personnel-protective environment, none disclose the employment of simple operative structure, such as a lever-clip device, which will enable locking of the catheter to the cannula assembly and also facilitate pushing the cannula hub off the housing or nose/guard components for the cannula when the latter is in its retracted position.

SUMMARY OF THE INVENTION

Accordingly, in order to facilitate a one-handed separation and relative manipulation of the catheter and cannula components of the intravenous catheter insertion device; especially the detachment from the catheter of the structure and elements containing the used cannula or hollow needle which was previously employed in forming the venipuncture, while permitting the catheter and thereto attached catheter hub, the latter of which comprise a part of a Luer lock lug or fitting, to remain in position at the site of the venipuncture, pursuant to the invention there is utilized a novel lever and clip arrangement which is positioned intermediate a housing for the containment of the cannula or needle, and including a nose guard projecting into the catheter hub, through the implementation of a simple one-handed manipulation of the lever and clip arrangement. This, in essence, renders simple the process of separating the catheter and cannula housing components by enabling a user to grip the housing structure containing the retracted used cannula and with one or more fingers of the same hand to manipulate the lever and clip so as to effectuate the release and pushing off of the catheter hub in a single motion.

Accordingly, it is an object of the present invention to provide a novel lever and clip arrangement enabling the separation of a safety catheter hub from a disposable cannula assembly.

Another object of the present invention is to provide a simple lever and clip structure mountable on the components of the intravenous catheter insertion device comprising a catheter hub of a safety catheter assembly and housing a nose guard structure adapted to receive a needle or cannula for forming the venipuncture in a patient, and whereby upon a simple manipulation of a clip or lever on the device which is operable with one hand of a user holding the device, it is possible to separate the components thereof to enable removal of the cannula and related components in a protective state while permitting the therefrom released and pushed-off catheter hub and thereto attached catheter extending into the venipuncture in the patient's body to remain in place.

BRIEF DESCRIPTION OF THE DRAWINGS

The foregoing and other objects and advantages of the invention may now be more readily ascertained from the following detailed description of various embodiments of the inventive device, taken in conjunction with the accompanying drawings; in which:

FIGS. 9 and 10 illustrate a catheter insertion arrangement in, respectively, operative and cannula-retracted positions thereof;

FIGS. 18 and 19 illustrate perspective views of another version of a catheter insertion device pursuant to the invention in, respectively, operative and cannula-retracted positions thereof;

DETAILED DESCRIPTION OF PREFERRED EMBODIMENTS

Figure 1:
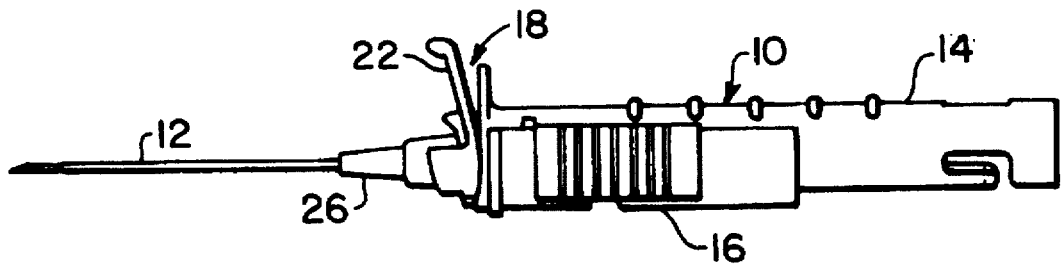
FIG. 1 illustrates an intravenous catheter injection device incorporating a lever and release clip structure pursuant to the invention.
Figure 2:
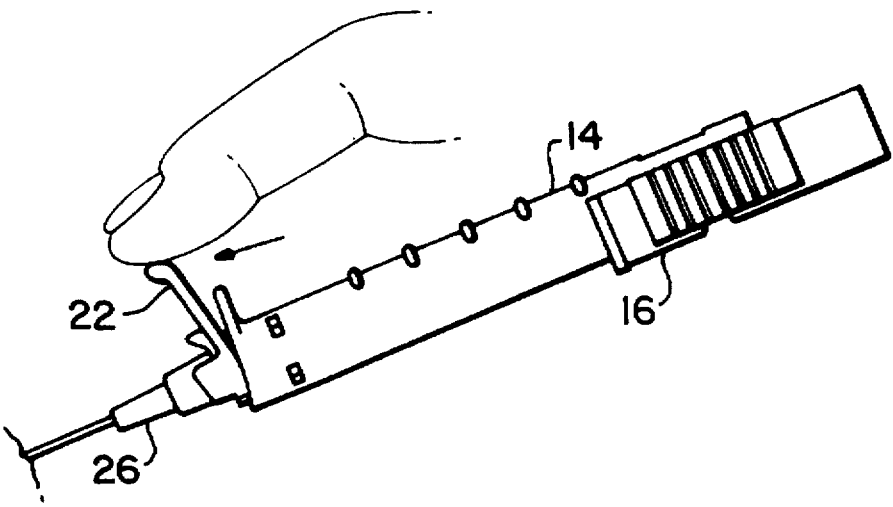
FIG. 2 illustrates the device of FIG. 1 in the process of being locked into operative position.

Referring in more specific detail to FIG. 1 of the drawings, there is illustrated an intravenous catheter insertion device 10 incorporating a catheter (not shown) having a cannular needle 12 projecting therefrom, wherein the needle is generally of surgical steel construction adapted to be inserted into the vein of a patient in the shown extended position thereof. The insertion device 10 includes a guard 14 and a housing 16, and wherein the structure thereof includes a nose section 18 comprising a snap-in nose 20. A lever and release clip 22 is mounted at the leading end of the guard 14 and, as shown in FIG. 2 of the drawings, the hub 26 of the catheter is adapted to be attached to the housing 16 in a locked position. In order to ensure that the locking position has been ascertained, an audible "click" may be generated upon locking. At this point the catheter hub 26 is locked in place, with the extended cannula 12 passing therethrough in extended position ready for venipuncture, and the catheter hub will not separate from the cannula assembly without any deliberate actions being imparted thereto by a physician or clinician. This, in essence, imparts a degree of a "fail-safe" operation to the catheter insertion device.

Figure 3:
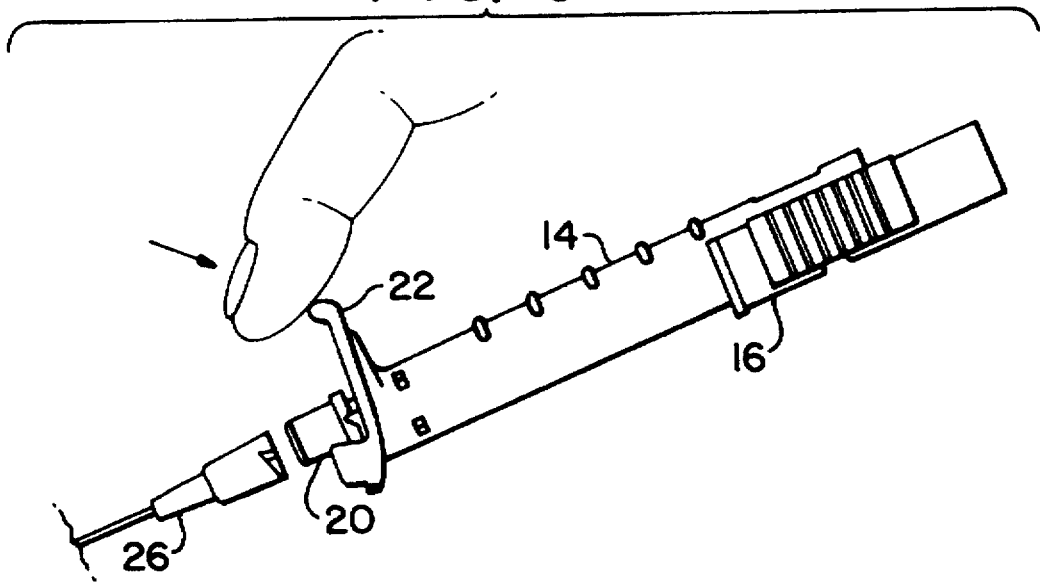
FIG. 3 illustrates the device of FIG. 1 in the process of the catheter hub being released from the cannula structure upon retraction of the cannula.

Upon the cannula 12 having been fully retracted into the protective housing 16, in order to separate the catheter and its catheter hub 26 from the remaining insertion structure, so as to remain in the vein of the patient, as is illustrated in FIG. 3 of the drawings, a user would push back and then down on the lever clip 22 with one finger, releasing the catheter hub 26 and concurrently pushing the latter off the nose guard and housing. It is also possible for the user of the catheter insertion device 10 to merely push off and release the catheter hub 26 by pushing forward somewhat harder on the clip tab 30 and, in the event the user is implementing a difficult catheter insertion into a patient, it is possible for him or her to release the catheter hub 26 prior to locking so as to impart a more sensitive "feel" to the insertion of the cannula 12 into the vein of the patient.

Figure 4A:
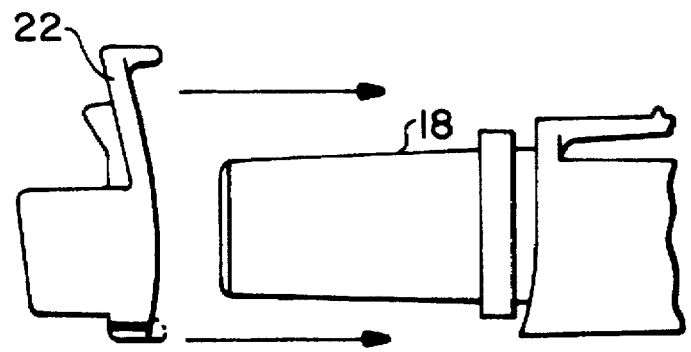
FIGS. 4a through 4f illustrate various successive steps in respectively the operation and assembly of the lever and release clip structure pursuant to the inventive device.
Figure 4B:
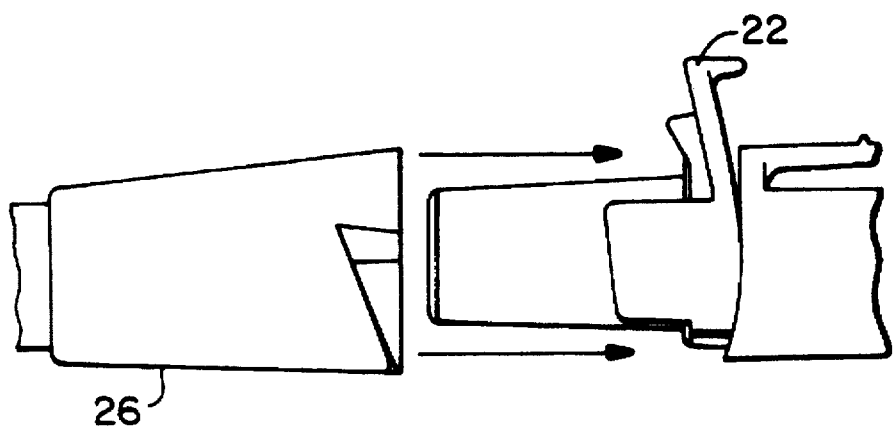
Figure 4C:
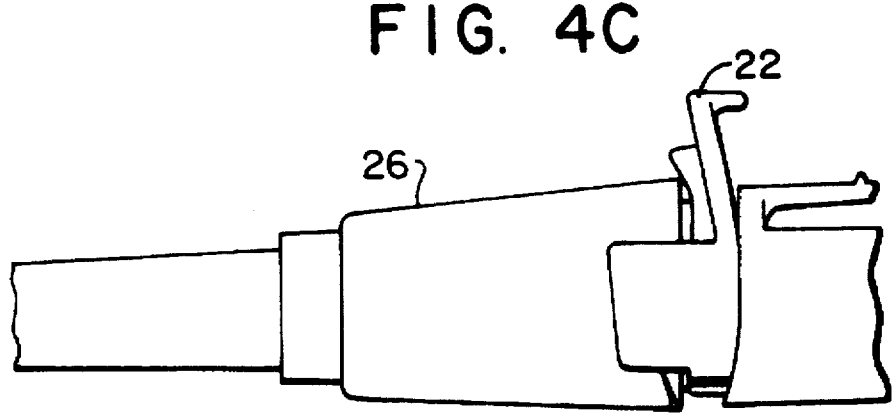

Referring to FIGS. 4a through 4c, there are shown successive steps in the assembly of the lever and release clip 22 of FIG. 1.

As shown in FIG. 4a, the lever-clip 22 is snapped onto the nose guard piece 18; and in FIG. 4b the properly oriented catheter hub 26 is then snapped onto the lever-clip and nose guard assembly. FIG. 4c illustrates the entire arrangement in the assembled and operatively locked condition thereof.

Figure 4D:
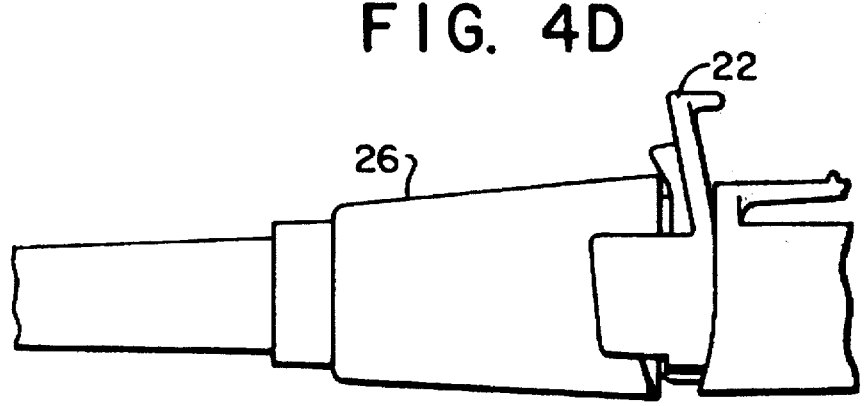

In order to release the catheter and its catheter hub 26 from the remaining cannula structure, as discussed with regard to FIG. 3 of the drawings, FIG. 4d illustrates the nose guard 18 being locked over the cannula point, with the cannula 12 or hollow needle (not shown) being in the fully retracted or guarded position within the housing structure 16.

Figure 4E:
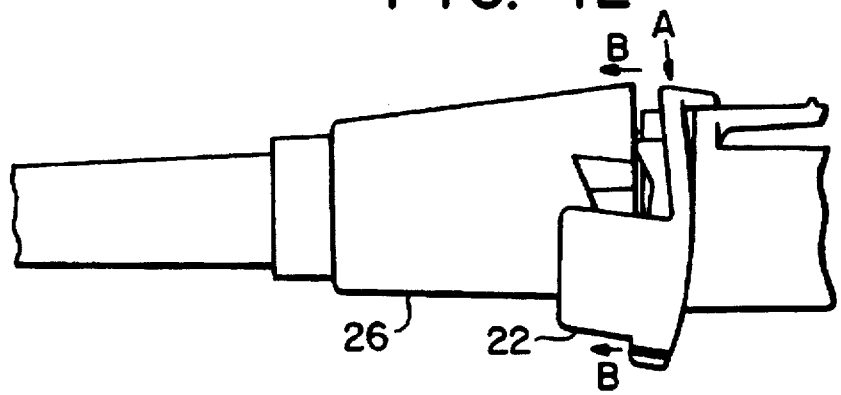
Figure 4F:
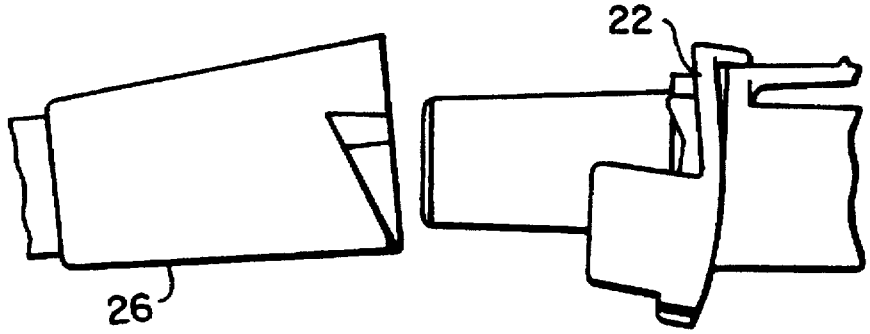
Figure 8:
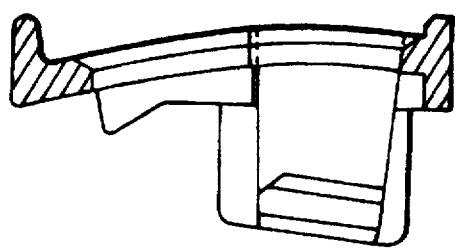
FIG. 8 illustrates a sectional view taken along Line 8—8 in FIG. 5.
Figure 7:
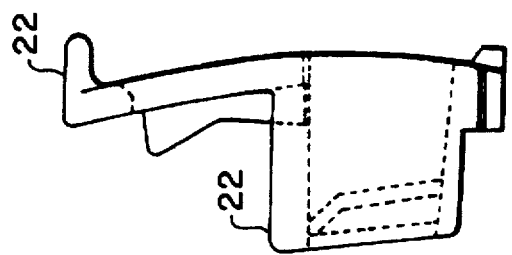
FIG. 7 illustrates a side view of the lever and release clip.
Figure 5:
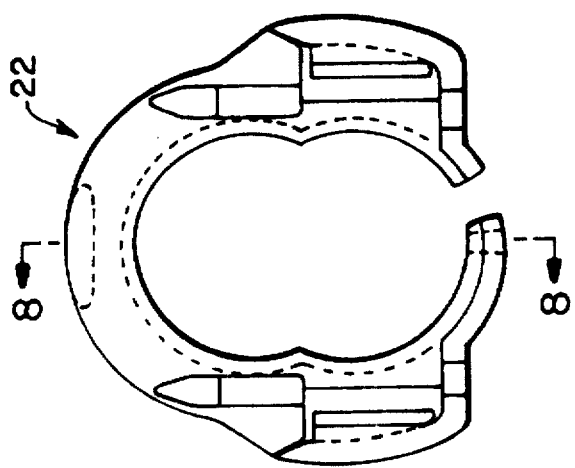
FIG. 5 illustrates a rear view of the lever and release clip.
Figure 6:
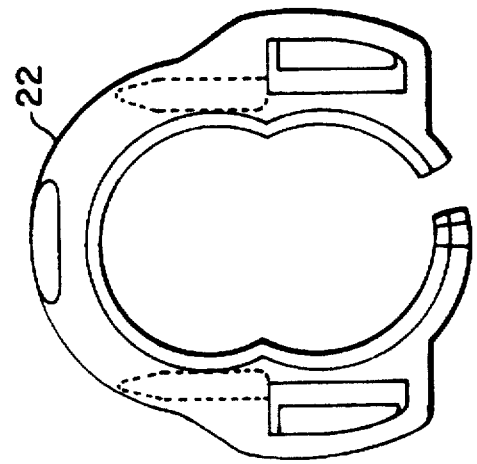
FIG. 6 illustrates a front view of the lever and release clip.

Thereafter, as shown in FIG. 4e of the drawings, the user or clinical personnel pushes downwardly on the lever clip 22 in the direction of arrow A, thereby both releasing and pushing off the catheter hub 26 as shown in the directions of arrows B.

Thereafter, with the catheter hub 26 and the attached catheter tube remaining in place, the latter having its leading or free end inserted into the vein of the patient, the cannula assembly comprising the nose guard 18, the housing 16 and lever clip 22 is removed and discarded.

As shown in FIGS. 5 through 8, the lever release clip 22 is constituted from a molded plastic material, preferably of a relatively soft plastic, such as polyethylene, having the nose guard formed thereon, in order to prevent any damage to the catheter hub Luer lock lugs during assembly therewith. This catheter insertion device 10, in essence, both releases and pushes off the catheter hub 26 when finger pressure is applied to the top of the lever clip 22, although the device is also capable of facilitating somewhat modified methods of catheter release; for instance, such as by pushing against and deflecting of the lever clip.

Referring to FIGS. 9 and 10, there are shown perspective views of a catheter insertion device 40, in which, as shown in FIG. 9, the cannula 42 projects from a nose guard 44 of a unitary structure, and extends from a housing 46, as known per se.

upon a lever clip 48 which is mounted on the nose guard 44 being tilted, as shown by arrow A in FIG. 10, the catheter hub (not shown) can be separated from the cannula assembly by simply pulling back on the lever clip or tab 44 of the nose guard. This tab portion 44 of the nose guard can be molded with an integral hinge to facilitate this type of function.

Figure 11:
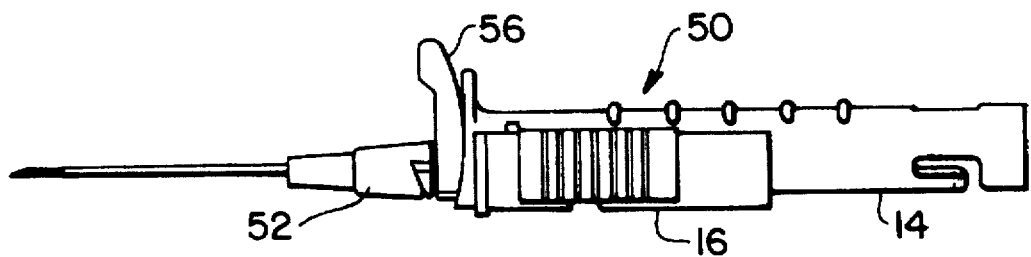
FIG. 11 illustrates a modified version of a lever and release clip structure on a catheter insertion device.

Referring to the catheter insertion device 50 in the embodiment of FIG. 11, in this instance there is also illustrated a modified version of a lever clip 56 wherein the catheter hub 52 is introduced into the lever clip opening and over the nose guard portion 54 as in the embodiment of FIG. 1 of the drawings.

Figure 12:
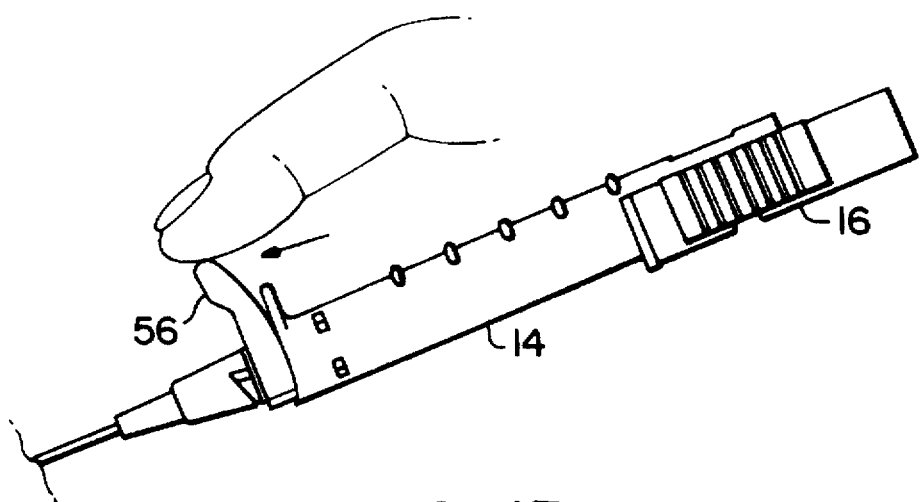
FIG. 12 illustrates the catheter insertion device of FIG. 11 in the process of being locked.

As shown in FIG. 12, this locking action is effected by pushing the lever clip 56 somewhat forwardly, generating an audible "click" to provide indication of such locking action having been implemented.

Figure 13:
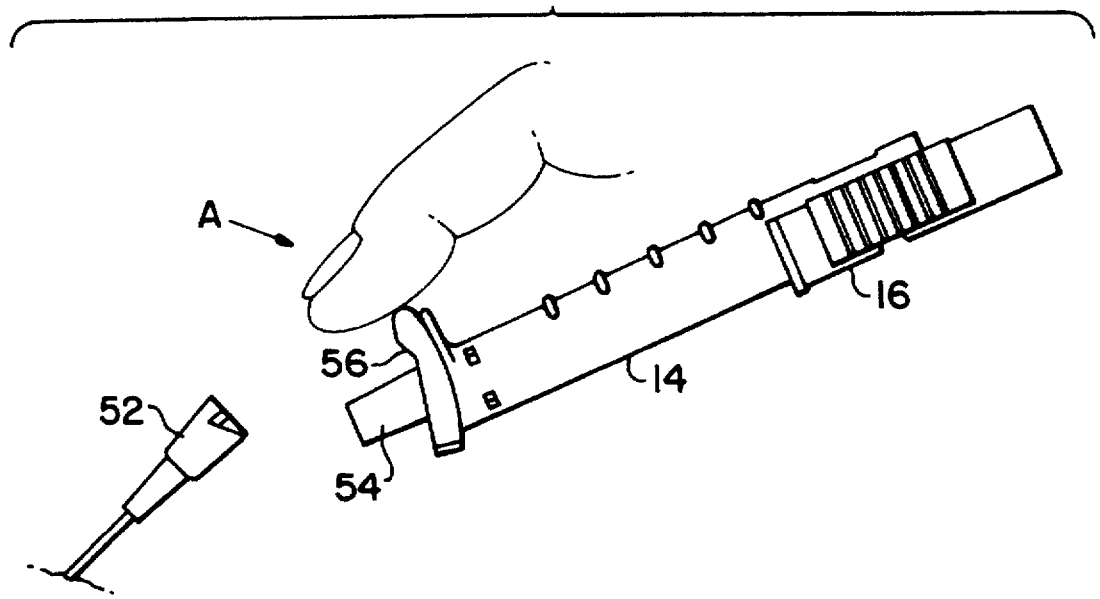
FIG. 13 illustrates the device of FIG. 11 in the process of being unlocked so as to separate the catheter hub from a nose guard portion of the device.

Conversely, in order to release the catheter hub 52 with the catheter tube from the cannula structure subsequent to locking, a user would simply pull back and/or down on the lever clip 56 as shown in the direction of arrow A in FIG. 13, thereby pushing the catheter hub off the nose. Other lever motions can of course also be contemplated herein.

Figure 14A:
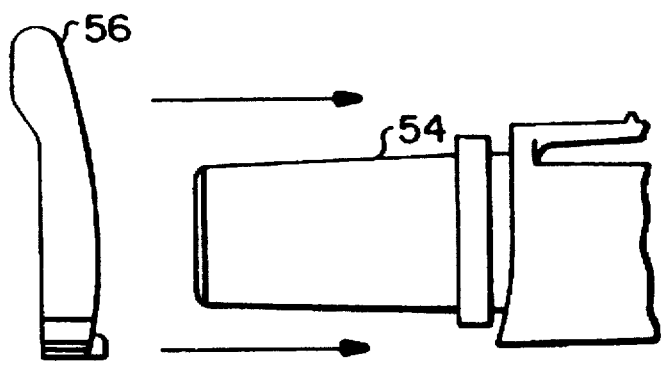
FIGS. 14a through 14c illustrate sequential steps in the assembly of the lever and release clip of FIG. 11.
Figure 14B:
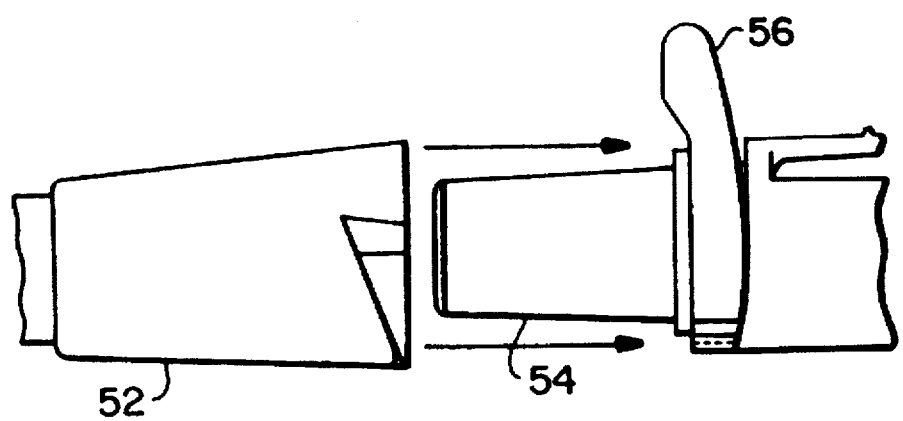
Figure 14C:
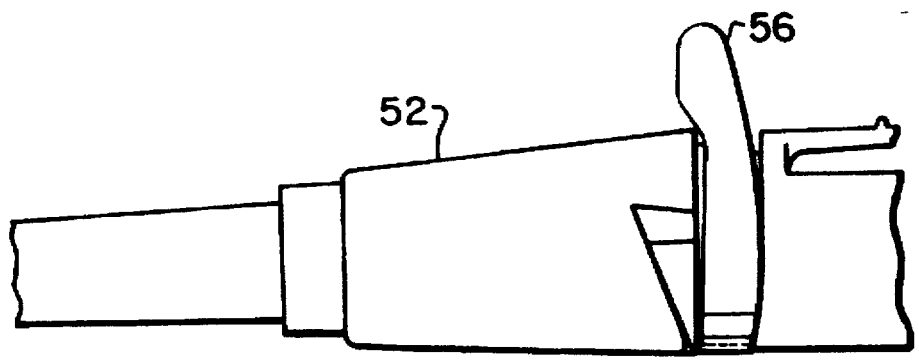

As shown in FIG. 14a through 14c, there are disclosed the successive steps in the assembly of the lever clip 56 of the device 50 of FIG. 11.

In FIG. 14a the lever clip 56 is oriented and snapped onto a rib formed on the nose guard portion 54 of the cannula structure. An unoriented catheter hub 52 is then pressed into place on the nose guard, as shown in FIG. 14b; and thereafter as shown in FIG. 14c, the entire catheter arrangement is in an assembled and operatively locked condition.

Figure 15:
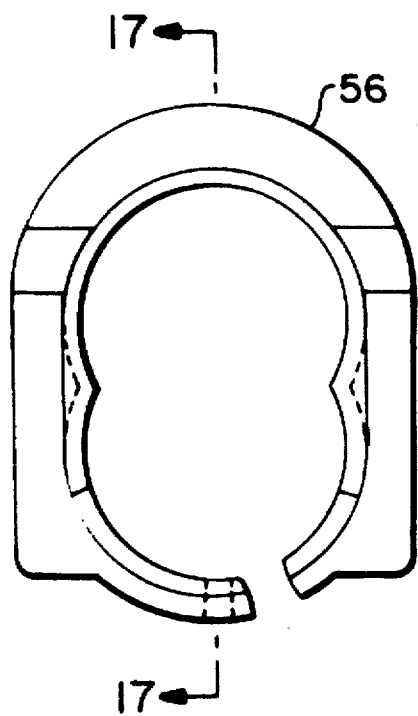
FIGS. 15, 16 and 17 illustrate, respectively, front, side and sectional views of the lever and release clip utilized in the embodiment of FIG. 11, FIG. 17 being a sectional view taken along Line 17—17 in FIG. 15.
Figure 16:
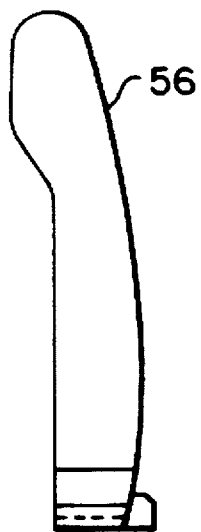
Figure 17:
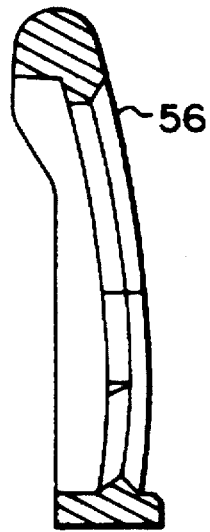

Illustrated in FIGS. 15 through 17 of the drawings is the configuration of the lever clip 56 showing the latter to be an essentially plate like structure having a central aperture 60 whereby, upon pulling back and/or pushing down on the lever-like structure of the lever clip, the catheter hub 52 is either pushed off or released from the nose guard portion 54 of the catheter insertion device 50. This particular lever clip structure does not require that the Luer lock lugs on the catheter hub 52 be oriented inasmuch as it pushes on the body of the hub and not on the lugs which are employed for forming a Luer lock connection subsequent to the withdrawal and detachment of the cannula structure. Inasmuch as this construction does not hold or release the Luer lock lugs on the catheter hub, any method which is currently employed for the release of the catheter can be utilized in addition to the above-described "one-finger" technique as shown in FIGS. 12 and 13 of the drawings.

Referring to the embodiment of FIGS. 18 and 19, illustrating in perspective view two positions of a catheter insertion device 70, whereby in FIG. 18 the cannula 72 is shown extended from the nose guard 74 and, in FIG. 19, is protectively retracted therein and into housing 76. This structure permits a user to utilize the same "one-handed" catheter separation techniques as previously mentioned, with the so-called push-tab/guard 78 being unlocked only when the nose guard 74 is locked thereby permitting pushing off of the catheter hub by exerting continuing finger pressure on the push tab 78.

Figure 20:
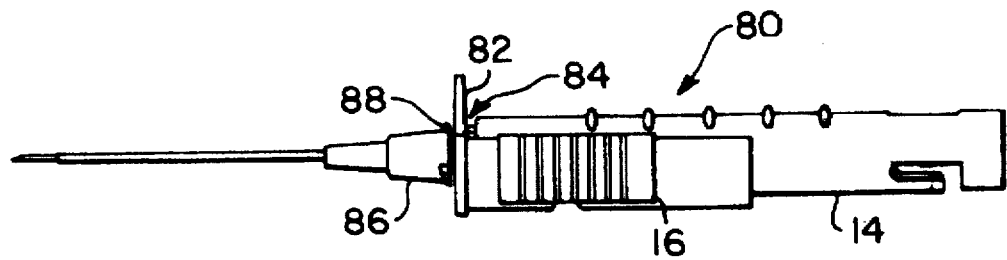
FIG. 20 illustrates another embodiment of a catheter insertion device utilizing a lever and clip structure.

As illustrated in FIG. 20 of the drawings, this is a somewhat modified version 80 of the previous devices with the exception being that the lever-clip arrangement 82 is integrally formed with the nose and guard structure 84.

Figure 21:
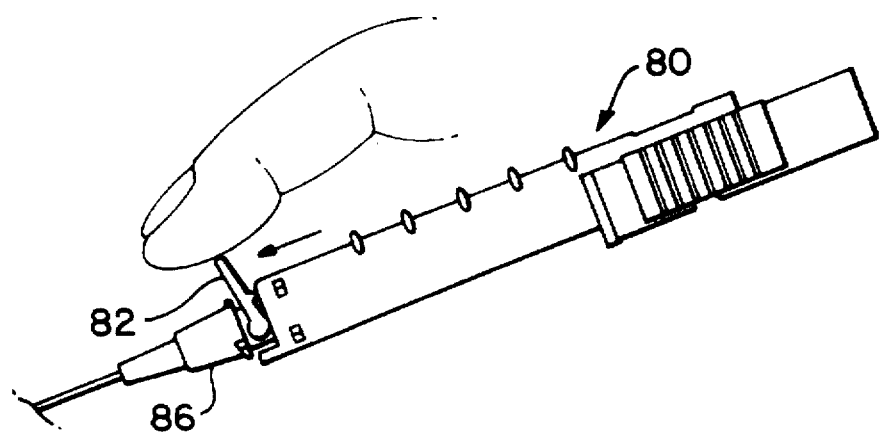
FIGS. 21 and 22 illustrate the device of FIG. 20 in, respectively, catheter locking and unlocking modes.

Hereby, the operation of locking the catheter hub 86 to the cannula structure as in FIG. 21 is identical to that as described with regard to FIG. 1, with an audible "click" noise signifying that a locking action has taken place.

Figure 22:
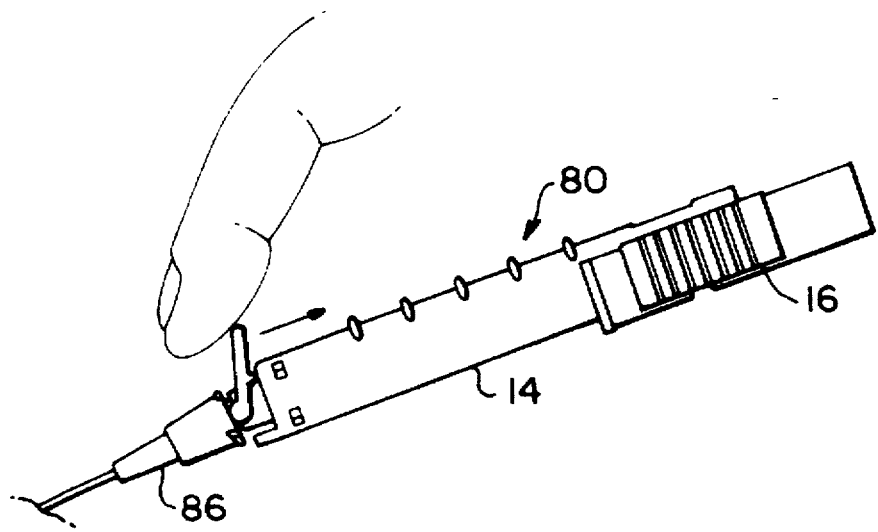

Conversely, as shown in FIG. 22, after locking of the catheter hub 86, the latter can be disengaged by any method currently employed as hereinbefore described. In addition, a user can pull back slightly on the push-tab 88 on the nose guard so as to disengage the catheter hub 86 from the cannula structure; in effect, providing for a "one-handed" operation.

Figure 23:
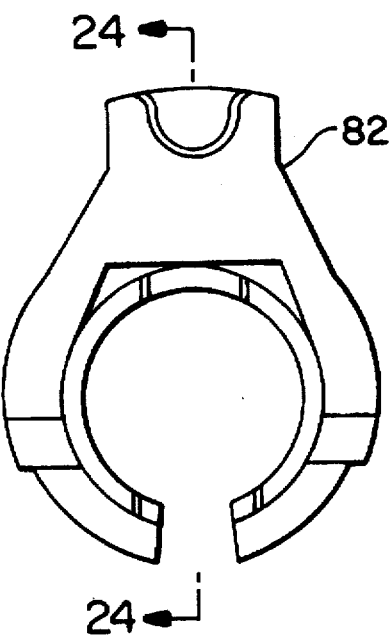
FIG. 23 illustrates a front view of the combined lever and clip and cannula guard structure utilized in the catheter device embodiment of FIG. 20.
Figure 24:
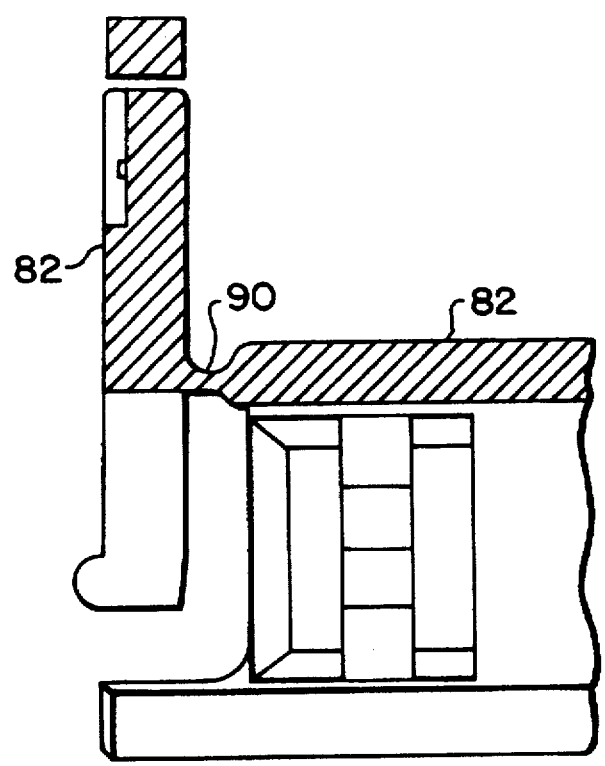
FIG. 24 illustrates a sectional view taken along Line 24—24 in FIG. 23.

As shown in FIGS. 23 and 24, the guard and snap-in nose portion 82 having the projecting lever 82 thereon are integrally molded, using a living hinge 90 to enable the lever portion, as shown in FIGS. 21 and 22, to be resiliently tilted in opposite directions so as to cause the contacting lower projecting end portion 92 thereof to be able to push the catheter hub 86 away from and off the remaining cannula structure, as shown in FIG. 22 of the drawings.

Figure 25:
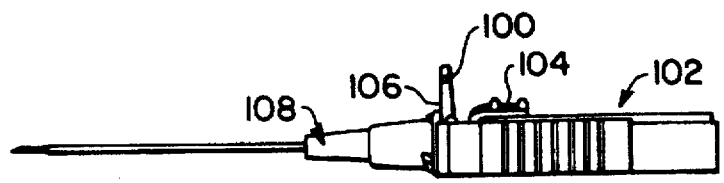
FIG. 25 illustrates a further modified catheter insertion device pursuant to the invention.
Figure 26:
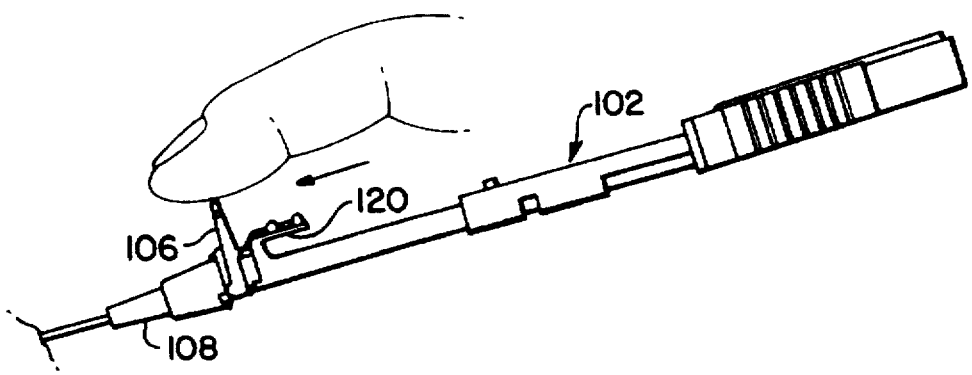
FIGS. 26 and 27 illustrate the catheter device of FIG. 25 in, respectively, the catheter locking and unlocking modes thereof.
Figure 27:
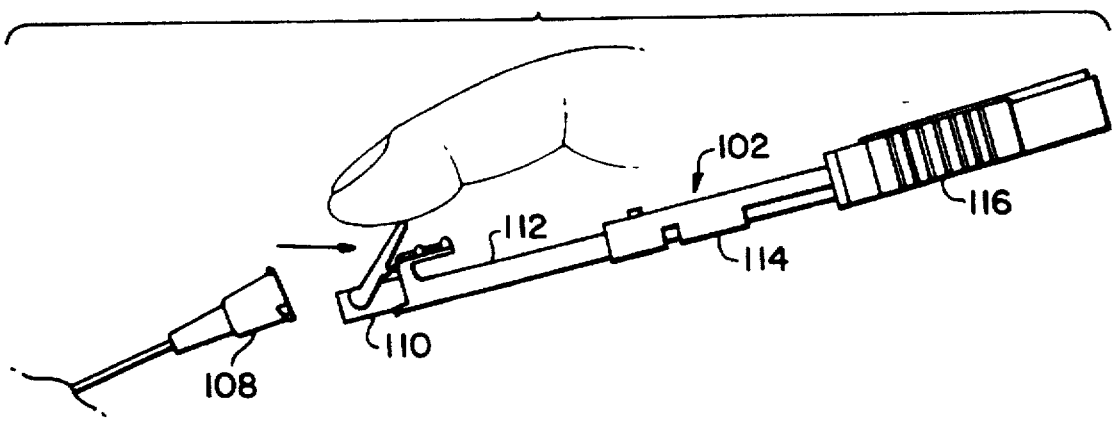

Similarly, as shown in FIGS. 25 through 27, the lever and structure 100 of this catheter device 102 is a simple one-piece or unitarily molded nose guard 104 having a protruding member 106 in the form of a tiltable lever whereby, as shown in FIG. 26, the forward movement thereof enables the catheter hub 108 to be locked into position onto the nose portion 110 of the cannula assembly 112, and with the extension of the telescoping arrangement 114, 116 for receiving the retracted cannula to be smooth and chatter-free in operation through the employment of a suitable lubricous plastic material.

The unlocking action for separating the catheter hub 108 and its attached catheter tube from the remaining cannula structure, whereby the cannula has been retracted into its protective position, can be implemented in a manner as described hereinbefore by simply pulling back upon the tiltable lever 106 as shown in FIG. 27. The user may also pull back slightly on the push tab 120 on the nose guard 104 to disengage the catheter hub 108 from the disposable cannula structure pursuant to the inventive "one-handed" operation of the device.

While there has been shown and described what are considered to be preferred embodiments of the invention, it will, of course, be understood that various modifications and changes in form or detail could readily be made without departing from the spirit of the invention. It is, therefore, intended that the invention be not limited to the exact form and detail herein shown and described, nor to anything less than the whole of the invention herein disclosed as hereinafter claimed.

What is claimed is:

1. A catheter insertion device, comprising:
   (a) a housing for receiving a cannular needle, said cannular needle extending from an end of said housing and being adapted to administer a catheter to a patient;
   (b) a needle nose guard slidably mounted on said housing, said cannular needle extending through said nose guard in the operative position of said cannular needle;
   (c) a catheter hub supporting structure being provided on said needle nose guard;
   (d) a catheter slidably mounted on said cannular needle, said catheter including a catheter hub engaged on said catheter hub supporting structure; and
   (e) a lever-clip means being arranged on said catheter hub supporting means, said lever-clip means being actuatable in at least one direction to facilitate locking of said catheter hub to said catheter hub supporting structure in the extended operative position of said cannular needle and being actuatable in at least one other direction subsequent to retraction of said cannular needle into a protective environment so as to release and push said catheter hub off said catheter hub supporting structure.

2. A catheter insertion device as claimed in claim 1, wherein said lever-clip means comprises a plate-shaped element mounted on said catheter hub supporting means.

3. A catheter insertion device as claimed in claim 2, wherein said plate-shaped element comprises a projecting tab member actuatable in response to pressure being exerted thereagainst by a finger of a user of said device.

4. A catheter insertion device as claimed in claim 3, wherein said housing includes at least one gripping surface engageable by the hand of the user possessing the finger for actuating said lever-clip means.

5. A catheter insertion device as claimed in claim 1, wherein said lever-clip means is molded from a resiliently deformable plastic material.

6. A catheter insertion device as claimed in claim 1, wherein said lever-clip means is integrally formed with said needle nose guard.

7. A catheter insertion device as claimed in claim 1, wherein said lever-clip means comprises a push-tab on said needle nose guard.

8. A catheter insertion device as claimed in claim 7, wherein said push-tab is integrally formed with said needle nose guard.

9. A catheter insertion device as claimed in claim 1, wherein said lever-clip means comprises a hub portion mountable on said needle nose guard, and lever means hingedly connected with said hub portion adapted to be resiliently deflected for pushing said catheter hub off the catheter hub supporting structure.

10. A catheter insertion device as claimed in claim 9, wherein said hub portion and lever means of said lever-clip means comprises a unitarily formed structure.

11. A catheter insertion device as claimed in claim 10, wherein said unitarily formed structure is constituted from a molded plastic material.

12. A catheter insertion device as claimed in claim 1, wherein said needle nose guard includes means for retracting said cannular needle into said protective environment.

13. A catheter insertion device as claimed in claim 1, wherein audible indication is provided relative to the positions of said cannular needle in said device.

* * * * *